US009668723B2

(12) United States Patent
Keating et al.

(10) Patent No.: US 9,668,723 B2
(45) Date of Patent: *Jun. 6, 2017

(54) LAPAROSCOPIC SYSTEM

(71) Applicant: neoSurgical Limited, Parkmore, Co. Galway (IE)

(72) Inventors: Ronan Keating, Moycullen Village (IE); Gerard Rabbitte, Tuan (IE); Barry Russell, Nass (IE)

(73) Assignee: NEOSURGICAL LIMITED, Galway (IE)

( * ) Notice: Subject to any disclaimer, the term of this patent is extended or adjusted under 35 U.S.C. 154(b) by 596 days.

This patent is subject to a terminal disclaimer.

(21) Appl. No.: 14/045,590

(22) Filed: Oct. 3, 2013

(65) Prior Publication Data
US 2014/0066953 A1 Mar. 6, 2014

Related U.S. Application Data

(63) Continuation-in-part of application No. PCT/EP2012/070345, filed on Oct. 12, 2012.

(30) Foreign Application Priority Data

Oct. 13, 2011 (GB) .................................... 1117711.0

(51) Int. Cl.
A61B 1/32 (2006.01)
A61B 17/00 (2006.01)
(Continued)

(52) U.S. Cl.
CPC .... *A61B 17/0469* (2013.01); *A61B 17/00234* (2013.01); *A61B 17/0206* (2013.01); *A61B 17/3423* (2013.01); *A61B 17/3439* (2013.01); *A61M 39/0247* (2013.01); *A61B 17/3462* (2013.01); *A61B 2017/347* (2013.01); *A61B 2017/349* (2013.01);
(Continued)

(58) Field of Classification Search
CPC .......... A61B 17/3423; A61B 17/00234; A61B 17/0469; A61B 17/3439; A61B 17/3462; A61B 2017/347; A61B 2017/349; A61B 2017/3492
See application file for complete search history.

(56) References Cited

U.S. PATENT DOCUMENTS 3,896,816 A * 7/1975 Mattler ............. A61M 25/1009
604/103.03
5,443,484 A * 8/1995 Kirsch ............... A61B 17/0281
604/164.04
(Continued)

FOREIGN PATENT DOCUMENTS

IE WO 2011128392 A1 * 10/2011 ......... A61B 17/0401
WO 96/36283 A1 11/1996
WO 2010141418 A1 12/2010

*Primary Examiner* — Zade Coley
(74) *Attorney, Agent, or Firm* — Schwabe Williamson & Wyatt, PC

(57) ABSTRACT

A laparoscopic surgical system configured for cooperation with a trocar is described. In one configuration, the system is configured to expand to accommodate trocars of varying dimensions. In another configuration, which is not necessarily exclusive of the first configuration, the system may function to provide an anchoring and closure system for use in laparoscopic surgery.

60 Claims, 15 Drawing Sheets

(51) Int. Cl.
*A61B 17/34* (2006.01)
*A61B 17/04* (2006.01)
*A61M 39/02* (2006.01)
*A61B 17/02* (2006.01)
*A61M 39/06* (2006.01)

(52) U.S. Cl.
CPC ............... *A61B 2017/3492* (2013.01); *A61M 2039/0279* (2013.01); *A61M 2039/0673* (2013.01)

(56) References Cited

U.S. PATENT DOCUMENTS

| | | | |
|---|---|---|---|
| 5,445,615 A | 8/1995 | Yoon | |
| 5,651,771 A * | 7/1997 | Tangherlini | A61B 17/3462 604/158 |
| 5,713,869 A * | 2/1998 | Morejon | A61B 17/3421 604/164.01 |
| 5,716,369 A * | 2/1998 | Riza | A61B 17/0469 606/139 |
| 5,792,112 A * | 8/1998 | Hart | A61B 17/3417 604/164.01 |
| 5,800,451 A * | 9/1998 | Buess | A61B 17/3421 604/167.03 |
| 5,814,065 A * | 9/1998 | Diaz | A61B 17/0469 112/169 |
| 5,993,471 A * | 11/1999 | Riza | A61B 17/3498 606/185 |
| 6,551,270 B1 | 4/2003 | Bimbo | |
| 6,908,454 B2 * | 6/2005 | McFarlane | A61B 17/3421 604/104 |
| 8,162,893 B2 * | 4/2012 | Okihisa | A61B 17/3421 604/165.01 |
| 2004/0054353 A1 | 3/2004 | Taylor | |
| 2005/0209608 A1 | 9/2005 | O'Heeron | |
| 2005/0222582 A1 | 10/2005 | Wenchell | |
| 2006/0149306 A1 | 7/2006 | Hart | |
| 2006/0247500 A1 * | 11/2006 | Voegele | A61B 1/32 600/208 |
| 2007/0088241 A1 | 4/2007 | Brustad | |
| 2007/0239108 A1 * | 10/2007 | Albrecht | A61B 17/3415 604/96.01 |
| 2008/0027476 A1 * | 1/2008 | Piskun | A61B 17/3403 606/185 |
| 2008/0097485 A1 * | 4/2008 | Shpaichler | A61B 17/3421 606/148 |
| 2009/0182282 A1 * | 7/2009 | Okihisa | A61B 17/3421 604/165.01 |
| 2009/0326465 A1 | 12/2009 | Richard | |
| 2010/0081881 A1 | 4/2010 | Murray | |
| 2010/0094228 A1 | 4/2010 | Bettuchi | |
| 2010/0100043 A1 | 4/2010 | Racenet | |
| 2010/0234689 A1 | 9/2010 | Wagner | |
| 2011/0144589 A1 | 6/2011 | Ortiz | |

\* cited by examiner

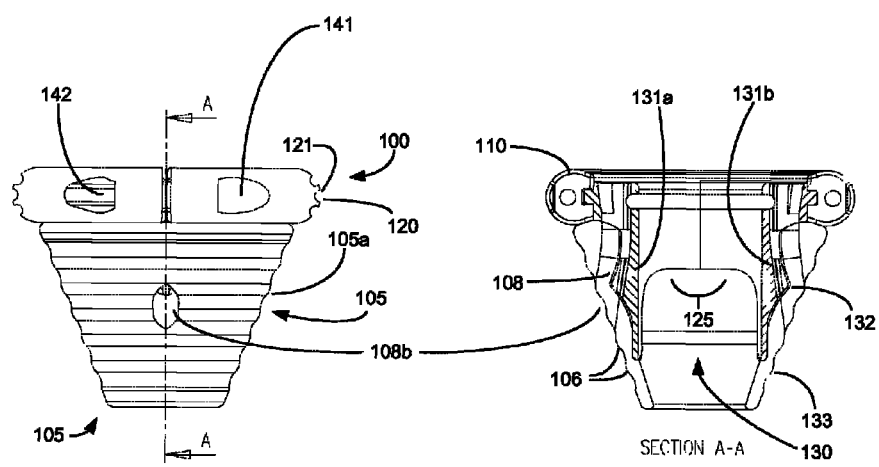
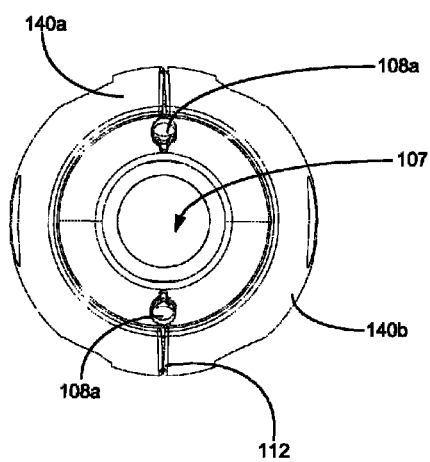
Figure 1A  
Figure 1B
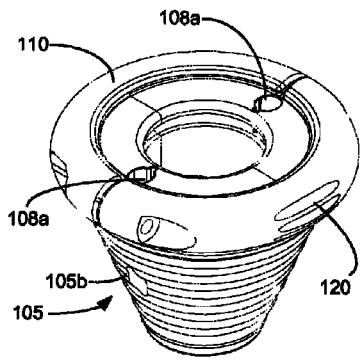
Figure 1C  
Figure 1D

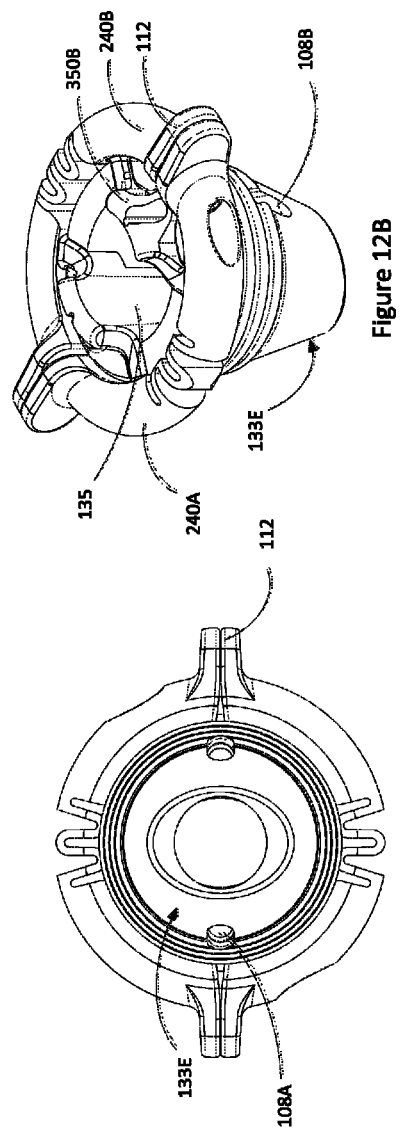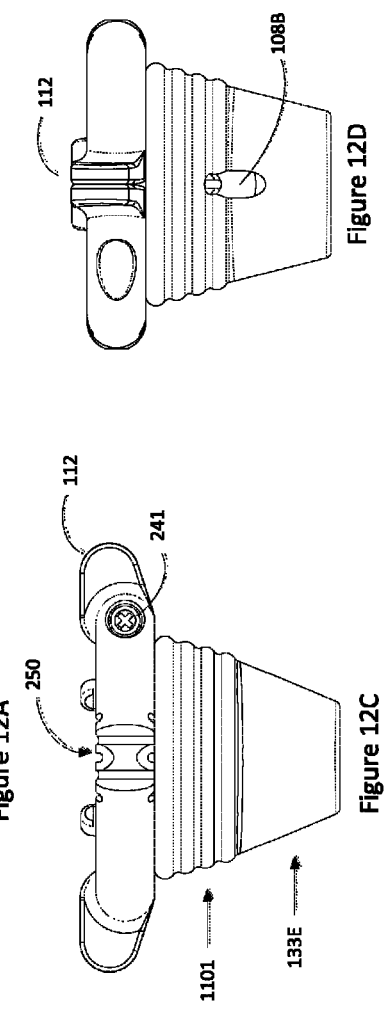

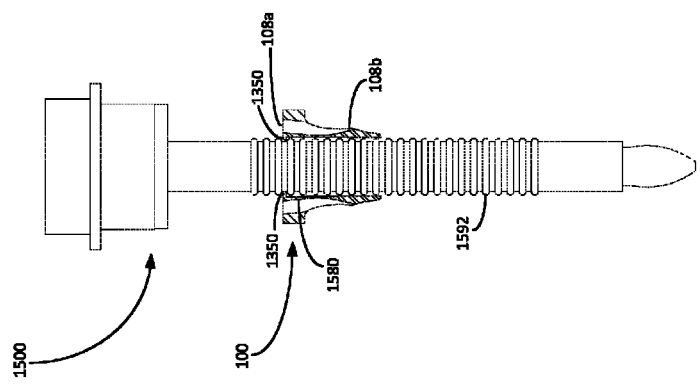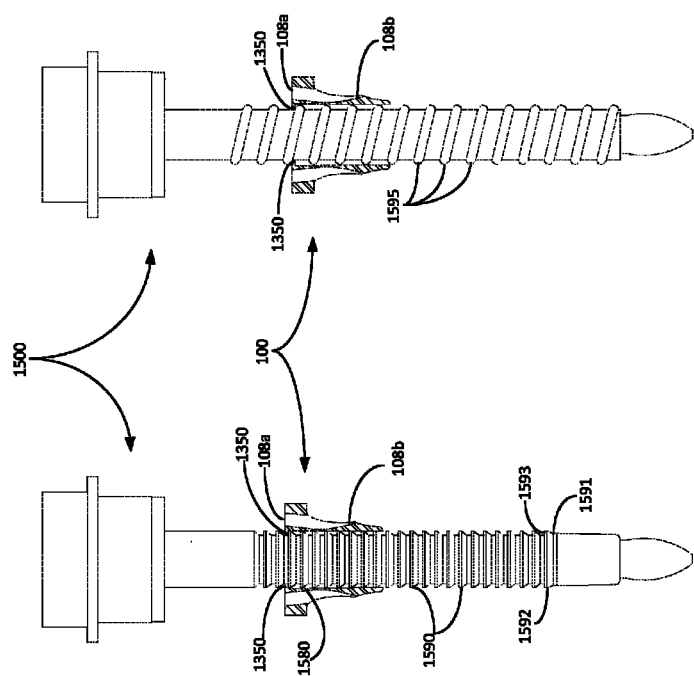

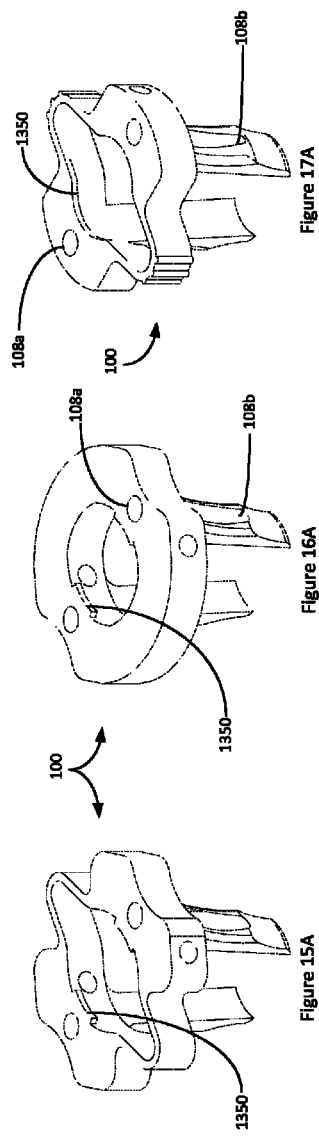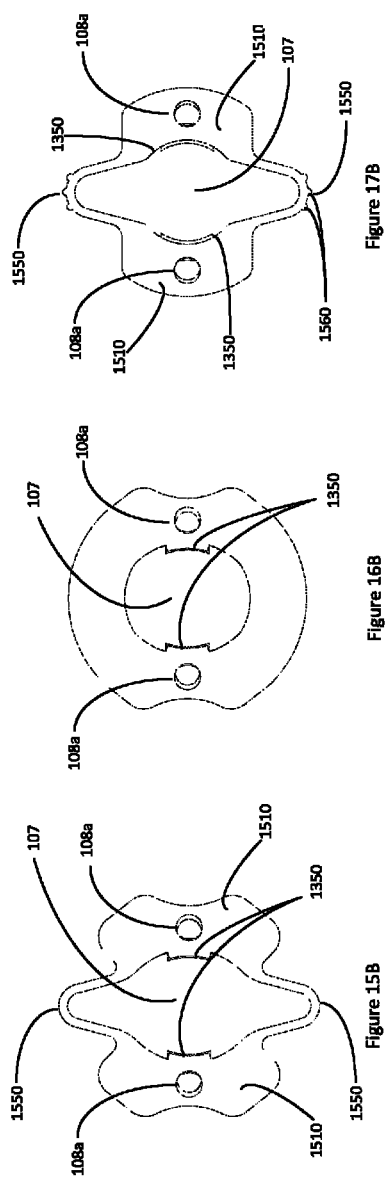

LAPAROSCOPIC SYSTEM

CROSS REFERENCE TO RELATED APPLICATIONS

The present application is a continuation-in-part of and claims priority to PCT Application No. PCT/EP2012/070345, filed on Oct. 12, 2012, entitled "LAPAROSCOPIC SYSTEM," which claims priority to GB Application No. 1117711.0, filed Oct. 13, 2011, entitled "LAPAROSCOPIC SYSTEM." The entire disclosures of both applications are hereby incorporated by reference in their entirety.

FIELD OF THE INVENTION

The present invention relates to laparoscopic systems and in particular to laparoscopic surgical systems configured for cooperation with a trocar. In one configuration, the system is configured to expand to accommodate trocars of varying dimensions. In another configuration, which is not necessarily exclusive of the first configuration, the system may function to provide an anchoring and closure system for use in laparoscopic surgery.

BACKGROUND

There are difficulties sometimes associated with the closure of the trocar wound site for example, in laparoscopic procedures. There are difficulties in particular in finding the fascia layer through which a suture must be passed to ensure good and adequate port site closure.

With deeper port sites, such as with an obese patient, it is often more difficult for the surgeon to gain deep access to the fascial layer to securely place a suture therein. In certain instances it may be necessary to cut open the wound to accurately place a suture fixation on the inner fascia layer.

The consequences of inadequate closure may be serious. For example, the patient may be subject to an early or late onset hernia, bowel stricture and/or bleeding from the port site. All of these complications have varying associated morbidities up to and including fatalities in serious undetected bowel strictures. The rate of port site herniation is widely published to be up to 3% for the normal population and double this for the obese cohort.

There are therefore a number of problems with current methods of trocar port site closure that need to be addressed, particularly for the obese patient.

There are further difficulties in anchoring or otherwise securing laparoscopic surgical devices relative to a laparoscopic surgical port, in particular with Hasson type ports. Suture stays can be difficult to manage during Hasson trocar sleeve or olive fixation and can become tangled when removing or adjusting the trocar. These problems also need to be addressed in order to ensure an efficient workflow for the surgeon.

Typically an olive or trocar sleeve is provided for a specific trocar type (Hasson) and the two are provided in co-operation with one another prior to any surgical insertion of the trocar into the abdominal wall. This is not always appropriate as not all surgery requires use of an olive at the start of the procedure, particularly off midline when utilizing radially dilating trocars. However, with excessive trocar manipulation, improved trocar anchoring and subsequent port closure may be required.

SUMMARY

These needs and others are addressed by a laparoscopic device in accordance with the claims that follow. In one aspect the device provides for deployment of a suture and anchor to enable port site closure subsequent to a laparoscopic surgical procedure which may be used to anchor the device during the laparoscopic procedure.

By providing an expandable housing whose inner diameter may be varied it is possible in accordance with the present teaching to accommodate surgical instrumentation such as trocars of different dimensions.

By providing the device having first and second parts it is possible, in accordance with one aspect to define a mouth within which a trocar can be presented sidewardly to the device so as to allow the mating of the device with a trocar subsequent to the insertion of the trocar into the abdominal wall.

These and other features of the present teaching will be better understood with reference to the drawings which follow which are provided to assist in an understanding of the present teaching and are not to be construed as limiting in any fashion.

BRIEF DESCRIPTION OF THE DRAWINGS

The present teaching will now be described with reference to the accompanying drawings in which:

FIGS. 1A to 1D show an olive and associated sleeve that may be used in accordance with the present teaching to provide for a closure of a laparoscopic port with FIG. 1A showing a side view, FIG. 1B a section along the line A-A of FIG. 1A, and FIG. 1C a plan view of the device of FIG. 1A, and FIG. 1D shows the device in isometric view.

FIG. 2D shows the device in isometric view.

FIG. 3D shows the device in isometric view.

FIG. 4D shows the device in isometric view.

FIG. 10A shows the device in a closed position and FIG. 10B shows the device in an open position.

FIGS. 12A to 12D show another example of an olive in accordance with the present teaching.

FIGS. 13A to 13C show examples of a system in accordance with the present teaching including locking surfaces configured to positively engage with a received trocar.

FIGS. 15A and 15B show examples of an olive in accordance with the present teaching.

FIGS. 16A and 16B show examples of an olive in accordance with the present teaching.

FIGS. 17A and 17B show examples of an olive in accordance with the present teaching.

DETAILED DESCRIPTION OF THE DRAWINGS

Figures 2A, 2B:
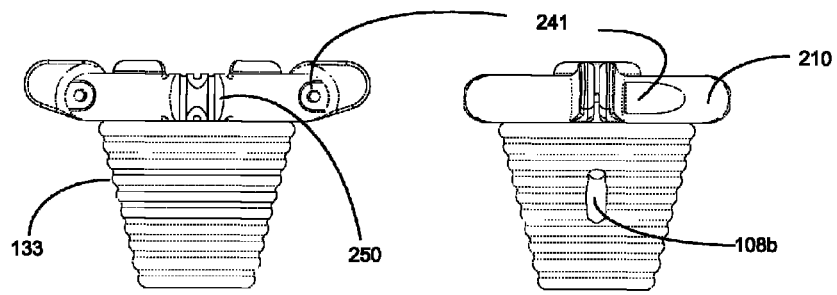
FIGS. 2A to 2D show another embodiment of an olive and associated sleeve that may be used in accordance with the present teaching to provide for a closure of a laparoscopic port with FIG. 2A showing a front elevation view, FIG. 2B a side elevation view of the device from FIG. 2A, and FIG. 2C a plan view of the device of FIG. 2A.
Figures 2C, 2D:
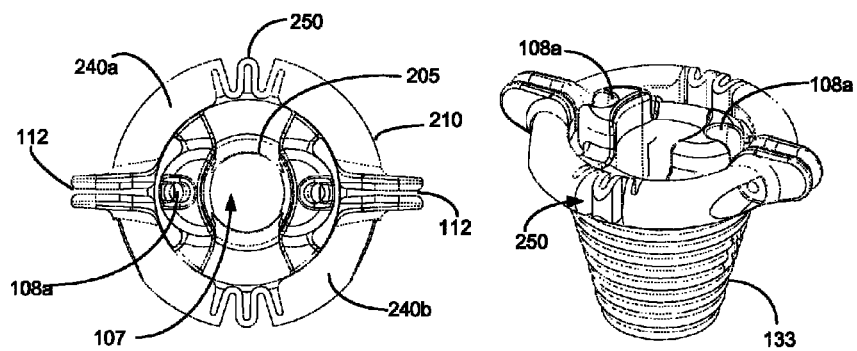

FIG. 1A shows a surgical device in the form of an olive 100 for use in laparoscopic surgery. As shown, the olive comprises a housing which in use may be anchored to an abdominal wall to define an entry port 107, as shown in FIG. 1C, for presentation of a trocar or surgical devices into the abdominal wall for enabling laparoscopic surgical procedures. The words "olive" and "housing" within the context of the present teaching may be used interchangeably. The olive 100 of FIG. 1A comprises an abdominal wall contacting or engaging portion 105 and an outer resting portion 110 which in use will rest against the outer surface of the abdominal wall.

In this exemplary arrangement the abdominal wall engaging portion 105 extends inwardly from the resting portion 110 and is defined by a hollow conical structure having side walls 105a that taper inwardly. Threads or ribs 106 are arranged about the side walls 105 and operably provide for an anchoring of the olive against the abdominal wall. In this exemplary arrangement the threads are parallel with one another and extend about the outside surface of the abdominal wall engaging portion 105. These threads could be inflatable or otherwise expandable so that the cone may be inserted with a lower profile smooth cone. The threads could then be deployed to anchor the olive in position.

While not shown, the threads could also run in a non-helical fashion, such as linearly descending to avoid conflict, or extend inwardly such that on their expansion would effect a downward movement of the olive.

The abdominal wall engaging portion of the sleeve 105 is desirably provided at a mid-point of the olive 100 such that the outer resting portion is arranged symmetrically about it. The olive 100 defines an aperture in the body of the outer resting portion 110 that extends through to the abdominal wall engaging portion so as to define a lumen 130 for allowing introduction of a trocar into the abdominal cavity.

In this configuration, the olive is intended to be used with suture so as to allow the olive be anchored to the abdominal wall. The suture could also be used for closure of the wound after completion of a surgical procedure. To facilitate the delivery of suture, the olive comprises at least one needle guide channel 108 provided in a side wall of the abdominal wall engaging portion 105. The needle guide channel 108 comprises an entry port 108a for a needle driver to be presented to the olive and an exit port 108b from which suture which is coupled to a needle or an anchor may be driven using the needle driver out of and away from the abdominal wall engaging portion 105. The exit port 108b is provided on an outer surface 105b of the abdominal wall engaging portion 105. The needle guide channel 108 is desirably configured to taper outwardly such that an anchor presented through the guide will be directed into the abdominal wall that is contacting the abdominal wall engaging portion 105. In a first configuration the channel 108 provides a convex path relative to the lumen 130 such that a needle driver will initially be presented towards the lumen 130 on insertion through the entry port 108a and will then be displaced away from the lumen prior to exiting through the exit port 108b.

The exit angle relative to the perpendicular is desirably a fixed angle which may be optimally configured between 5 and 30°, or more preferably between 10 and 20°.

By providing a needle guide channel, suture can be coupled to respective anchors and directed into the abdominal wall. The anchor is desirably biased inwardly through the guide 108 using an anchor driver. The exit hole port 108b is desirably located such that the needle will pass into the subcutaneous layer of the abdominal wall. Desirably application of continued downward pressure using the needle driver will cause the anchor to then pass into the abdominal cavity, pulling suture with it.

On passage of the anchor into the abdominal cavity it will desirably hang, suspended on its suture, after the anchor driver is removed. The orientation of the anchor will typically change orientation from a vertical disposition used in the deployment configuration to a horizontal configuration. This may be assisted by coupling the suture to an anchor at a mid-point of the anchor such that it will pivot relative to the coupling to change its orientation. Anchoring is effected by retracting the deployed suture. This causes the suture to be pulled back into the olive, tightening the anchor against the inner abdominal wall. As the orientation of the needle has changed, it will not tend to retreat back through the abdominal wall through the path it developed on penetration of the wall. The olive is then resting against the outer surface of the abdominal wall and is prevented from moving away from that position through the action of the anchors against the inner surface of the abdominal wall. It is self-anchored. The retention of the position is maintained in this configuration by use of a suture cleat 112 within which the suture can be tightened against. In the configuration of FIGS. 1A-1D, first and second needle guide channels 108 are provided, each being adjacent to their respective guide channel. The guide channels 108 are provided opposite to one another, in this configuration each are displaced about 180° away from the other.

It will be understood that this suture cleat 112 is an example of a suture securement feature provided adjacent or proximal to each of the entry ports 108a and being useable to secure the suture once tightened against the olive, thereby self-anchoring the olive relative to the abdominal wall. The cleat comprises two opposing faces which when brought together form a double taper to which a suture may be presented and tightened within. In this way the suture securement feature operates as a jam cleat. These faces may be textured or otherwise treated to improve their suture retention properties.

The olive may be provided with one or more contoured surfaces providing finger grips 120. These allow an operator to manually manipulate the olive without slipping. As is shown in FIG. 1A, these finger grips may comprise one or more projections or ribs 121 that extend beyond the normal surface of the outer resting portion 110 so as to provide a proud contact surface for gripping by an operator.

It will be appreciated that anchoring may take some time. To provide for a temporary location of the olive, adhesive pads may be provided on the lower surface which will temporarily bond with the surface of the body and allow for the deployment of the needles to adopt a more permanent secondary anchoring.

On completion of the surgical procedure, the deployed anchors and sutures may be used to effect a closure of the wound. The suture is released from its suture cleat 112 and the olive is retracted from the abdomen. The surgeon may then tie a knot, and use the still tethered suture to effect a closure of the wound. Desirably sutures and/or needle anchors are bioabsorbable so as to allow for their eventual dissolving after the procedure.

An alternative method of use would be to deploy the anchors as described above. To close the wound the anchors could be picked by a grasper disposed through a trocar while the spools are in the unlocked position. The anchors are removed through the trocar; the two suture ends are tied or mated and passed through the trocar again to create a closed loop of suture. This joining process could also be completed internally. The olive would then be removed and the suture trimmed and knotted as described above.

It will be appreciated that the longer the length of the abdominal wall engaging portion 105, the less freedom a surgeon has during the laparoscopic procedure to manipulate his laparoscopic tools which are accessing the internal cavity through the device. By maintaining the abdominal wall engaging portion 105 as a shallow element more freedom is provided to the surgeon.

The abdominal wall engaging portion 105 may be provided as a rigid element. In another configuration it may be formed from a flexible, for example elastomeric, material. This would allow the wall engaging portion to deform to adapt to the contours of the abdominal wall with which it engages. While it may be advantageous to have this abdominal wall engaging portion 105 integrally formed with the olive proper, in certain configurations, the olive comprises a removable skirt or sleeve that is received over the projecting legs 131. Such an arrangement is the arrangement of FIG. 1B whereby the legs 131 comprise a projecting rib 132, over which a sleeve 133 is received. Due to the deformable material from which the sleeve 133 is formed, it expands and then retracts about the rib and is, through this engagement, retained in place. The provision of such a removable sleeve provides flexibility where for example the use of tissue invagination zones 125 is not required, such as when a Hasson or open cut down technique is utilised.

As shown in FIG. 1B, the sleeve 133 desirably is contoured or ribbed on its outer surface to define a plurality of displaced abutment surfaces which in use will restrict movement of the olive relative to the abdominal wall within which it is located.

The olive in this configuration is formed from first and second parts or portions, in this case two identical halves 140a, 140b, which are brought together to define a complete device. The portions are coupled together to form a complete circle defining the lumen 130. The outer resting portion 110 extends circumferentially about the entry port 107 and the diameter is fixed. On coupling the two portions together they may then be retained in position using for example first and second couplers. Examples of these couplers include a bolt and nut arrangement whereby a bolt is passed through a recess 141 provided on one portion to a recess 142 in the other portion where it is secured using a bolt. The recesses typically extend in a direction transverse to the longitudinal axis of the lumen 130.

FIGS. 2A-2D & 3A-3D each show a modification to the olive of FIGS. 1A-1D whereby the diameter of the outer resting portion is not fixed. Similar reference numerals are used for the same components to that described previously. In this configuration an outer resting portion 210 of the olive is expandable to increase the inner diameter of the outer resting portion so as to accommodate trocars of differing diameters. This is provided by a movement of the first and second portions relative to one another. Traditionally an olive is provided for use with a dedicated trocar of a fixed diameter. By providing this expandable olive, the present inventors have provided an olive which can be used with a variety of different trocars, dependent on the application.

Similarly to that described previously the outer resting portion 210 is provided as first and second portions 240a, 240b. On presentation of the two portions, which again are identical in form to one another, a complete circle is provided. The surfaces of the outer resting portion 210 extend circumferentially about the entry port 107 whereby a trocar may be presented to the lumen and pass into the abdominal cavity. The portions 240a, 240b are coupled to one another. They may be retained in location using for example a self-tapping screw that is presented through a recess 241 provided on a first portion to engage with the second portion. Other forms of coupling and retaining the portions may be advantageously employed.

To allow for expansion of the outer resting portion, in this configuration expansion struts 250 are provided. While these are shown on each of the first and second portions 240a, 240b and this advantageously allows for each of the two portions to expand to the same level so as to retain a level of symmetry about the lumen, other configurations may use one or more expansion struts 250. As they are expanding, they are moving relative to one another. It will be further appreciated that the expansion struts are an example of a concertina arrangement whereby the length of the circumferential path of the outer resting portion of the olive may be varied. Other arrangements including for example forming the outer resting portion at least in part from a deformable material will also allow for the varying of this circumferential path to accommodate trocars of different diameter. By providing first and second expansion struts on opposing sides of the lumen and configuring each to extend linearly on extension, it is possible to ensure that the needle guide channels are retained substantially opposite to one another irrespective of the length of the perimeter of the resting portion 210. The extension of the expansion struts is desirably operably in a substantially horizontal direction. In the provided configuration the expansion struts resemble a W shape, in another embodiment the struts may resemble an M shape. Further, the number, length and thickness of the struts may be varied to achieve different performance characteristics. The diameter between the struts may also be varied to adjust the stiffness of the struts and facilitate a range of expansions In a first configuration, the diameter of the outer resting portion 210 is dimensioned to accommodate the smallest diameter trocar with which the olive is intended to be used.

Presentation of anything larger than this minimum sized trocar will result in an expansion of the resting portion 210 sufficient to accommodate same.

In a similar fashion to that described with reference to FIGS. 1A-1D, the outer resting portion or collar may be coupled to a sleeve 133 which forms at least part of the abdominal wall engaging portion 105. The sleeve is provided with an annular ring 205 located at the end of the sleeve furthest from the outer resting portion. The dimensions of this ring 205 are chosen so as to provide an interference fit with the smallest compatible trocar and the largest. The ring will typically be sized to fit normally about the smallest diameter trocar (preferably 10-14 mm, ideally 13 mm) and on use with a larger diameter trocar (preferably 15 to 20 mm, ideally 17 mm) will expand to accommodate same. This expansion may result a lower portion of the sleeve adopting a substantially planar form, such that the sleeve 133 will taper from the outer collar 210 inwardly to about the needle exit port 108B and then adopt a substantially planar form parallel to the longitudinal axis of the lumen. It will also be observed from FIG. 2B that the dimensions of the exit port 108B in FIG. 2B are substantially larger than the corresponding exit port in FIGS. 1A and 1B. This increase in dimension is to compensate for any compression that would otherwise occur during an expansion of the sleeve.

The choice of durometer of the material chosen for the sleeve 133 will dictate the grip on the maximum and minimum sized trocars and will be optimised to provide a stable grip on compatible trocars during instrument exchange. The annular ring 205 provides both a sealing and trocar retention function and desirably is configured to accommodate a variety of trocar diameters and surface finishes. It will be appreciated that the diameter of the annular ring is desirably less than the outer diameter of the trocar such that when a trocar is presented through the ring, the ring provides a tight seal about the trocar. For example a ring having a diameter of 11 mm could be usefully employed with trocars of outer diameters in the range 13-17 mm. The compression of the ring around the trocar also provides for retention of the trocar in situ. As the ring is desirably made from a low durometer elastomer it has a level of tackiness that engages with the trocar to prevent the trocar slipping during use.

The olive is configured to be used with a needle driver and anchor, similarly to that described above with reference to FIGS. 1A to 1D. When the anchors are pulled taut, the grip that the sleeve exerts on the trocar is increased by compression of the sleeve. The level of grip can be altered by varying the durometer of the chosen material or the tension on the suture/anchor when cleated. The sleeve also functions as a seal in the Hasson indication where the compressive seal prevents $CO_2$ from escaping from an insufflated abdomen.

In a further modification to the arrangement illustrated in FIGS. 3A to 3D, the expansion struts 250 could be removed so that two portions, each providing a single channel and cleat moulding, 340a, 340b are provided. These are insertable into the sleeve where expansion would then be achieved solely by action of the trocar onto the sleeve.

Similarly to that described with reference to FIGS. 1A to 1D, the first 340a and second 340b portion each comprise legs 131a, 131b that project parallel to the intended longitudinal axis of the lumen 130. The legs define an abdominal wall engaging surface which comprises first and second cut-away portions provided in faces transverse to the exit ports of the needle channels. These cut away portions define a tissue invagination zone 125 within the abdominal wall engaging portion into which, in the absence of a covering sleeve, tissue may extend inwardly towards the lumen. It will be understood that this further assists in securing the olive relative to the abdominal wall and trocar as the ingress of the tissue within the tissue invagination zone 125 restricts a rotation of the olive relative to the abdominal wall The first and second portions are coupled together using a nut and bolt or self-tapping screw arrangement. In a modification to that of the previous described arrangements the recesses and associated screw paths 341a, 341b on each of the two portions are offset from one another. In this way, when the two portions are brought together and tightened, the coupling is symmetrical.

To prevent the legs 131a, 131b from kicking out when used with larger trocars, the configuration of this arrangement comprises a biasing element which acts on the legs to retain each of the two legs parallel to the other when engaging with a large diameter trocar. This is particularly important where the olive is used without the sleeve 133, the presence of the sleeve otherwise providing this biasing force acting to prevent the legs displacing away from the longitudinal axis of the lumen. The biasing element may be provided as a separate element to the legs or could be integrated onto the legs for example by overmoulding the legs with a resilient material which will bias the otherwise rigid legs to adopt a substantially parallel form. It will be seen from close inspection of FIG. 3a that in certain configurations the legs 131 are initially formed so as to bias inwardly towards the longitudinal axis of the lumen. This will ensure that when the sleeve is mated with the legs 131 that the action of the sleeve will serve at most to bring the legs into a parallel configuration and improve retention of the trocar within the olive. The legs may be overmoulded, or otherwise provided, with an elastomeric portion at their tip to further enhance trocar retention.

In the arrangement of FIGS. 3A to 3D, this biasing element is provided by extending the length of the legs so as to provide a projection 350 above the main surface 345 of the outer resting portion 340.

As was shown in the previous figures but has not yet been discussed, each of the legs 131 desirably also include an arcuate inner surface 135 which is shaped or contoured to mate with the contours of the trocars with which the olives are being used. Similarly to that discussed previously, the legs may be provided with ribs 132 that cooperate with and couple the legs to the sleeve as appropriate. In the absence of use of the olive with the sleeve, these ribs would operably couple with the fascia layer of the abdominal wall and retain the olive in position.

Figure 3A:
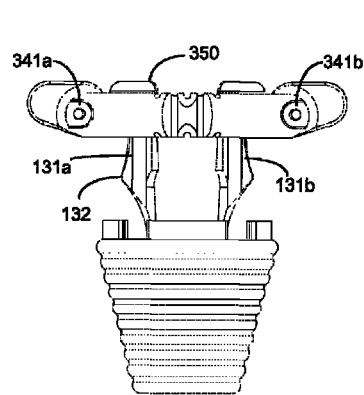
FIGS. 3A to 3D show an embodiment of an olive and associated sleeve, with the sleeve disengaged from the olive, where FIG. 3A showing a front elevation view, FIG. 3B a side elevation view of the device from FIG. 3A, and FIG. 3C a plan view of the device of FIG. 3A.
Figure 3B:
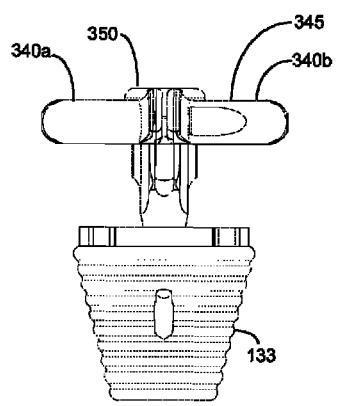
Figure 3C:
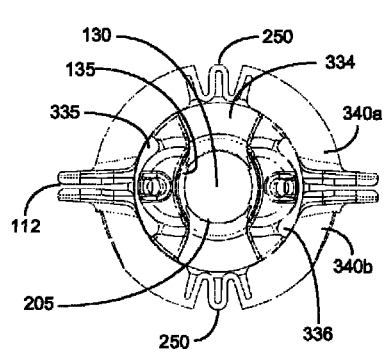
Figure 3D:
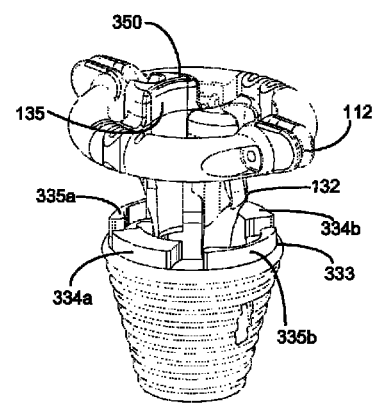

To ensure maintenance of coupling of the sleeve with the outer resting portion 340, each of the two are optimally configured to engage with one another. In the configuration of FIG. 3D an upper surface 333 of the sleeve is provided with a plurality of projections 334, 335 which are arranged circumferentially about the upper surface 333. In the configuration of FIGS. 3A to 3D, four projections are provided in two sets of two different dimensions. A first set of projections 335 engage with the outer resting portion and as shown in FIG. 3C are sized to fit in a similarly shaped recess 336 in the outer resting portion. When the self-tapping screw or other coupler is placed in the olive it pulls together the suture cleats and also reduces the area which receives the sleeve providing a fixation between the outer resting portion and sleeve. This ensures the sleeve remains in place when a trocar is passed though the olive and sleeve. The second set of projections 334 are dimensioned to occupy the space between the legs 131 and serve to prevent rotation of the sleeve relative to the outer resting portion.

FIG. 4 shows another configuration which similarly to that described previously provides an olive having legs 131 which are dimensioned and configured to cooperate with a trocar so as to retain the trocar in a desired orientation. In these configurations, the design is such that the legs provide an interference fit on a minimally sized trocar which obviates the need for an o-ring or other retention feature within the olive. This allows the user to place the olive on the trocar shaft and prevents the olive from falling off.

In the arrangement of FIGS. 4A to 4D, finger grips 420 are provided on an outer surface of the outer resting portion 440 and resemble a plurality of cogs. The grips function to assist a surgeon in manipulation of the device during use.

When the first and second portions 440*a*, 440*b* are brought together, the legs come together to define a complete trocar engaging lumen 450. In this arrangement, the trocar engaging lumen is made from an expandable material so as to form an expandable ring. The outer ring or collar (the outer resting portion), cleats and needle guide channel of the olive may all be made from a more rigid material, which is overmolded onto or otherwise coupled with the expandable ring 450. An inner surface 451 of the expandable ring 450 features longitudinal ribs 452 which reduce the surface contact with the soft material, to reduce friction and ease insertion of the trocar. The construction geometry of this ring could alternately be corrugated on both the inner and outer surface, to improve the expansion of the ring 450. It will be understood that the provision of this corrugated surface is one way of achieving additional flexibility in an otherwise more rigid structure and other ways could be utilised. The corrugated surface also serves to reduce the points of contact and so the friction with interoperating trocars or surgical instruments.

It will be appreciated from the plan view of FIG. 4C, that similarly to that described with reference to FIGS. 3A to 3D, that a space 460 between the legs may be provided to cooperate with locators from a sleeve, if the olive is used with a sleeve. These locators could fit directly into the space defined between the legs. In another configuration the locators could include some element of overlap as shown in FIG. 4F such as a shoulder 475 that would actively engage with a recess 470 on the main body of the olive housing to improve the inter-connection between the parts.

Similarly to that described with reference to previous figures, the first and second portions that co-operate to define the olive may be secured together using screws, nuts & bolts or the like. If a bolt head and nut are used, recesses 141, 142 are typically provided. The tightening of the two portions to one another also serves to tighten the suture cleats 112.

Figure 4A:
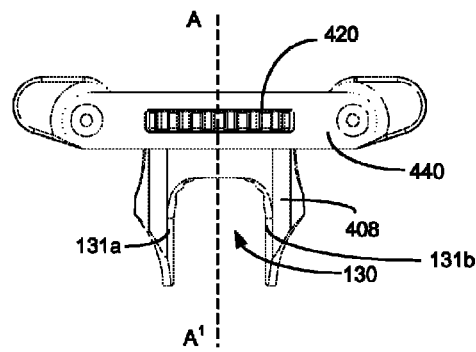
FIGS. 4A to 4F show a further embodiment of an olive that may be used in accordance with the present teaching to provide for a closure of a laparoscopic port with FIG. 4A showing a front elevation view, FIG. 4B a side elevation view of the device from FIG. 4A, and FIG. 4C a plan view of the device of FIG. 4A.
Figure 4B:
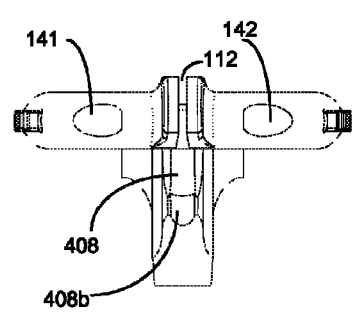
Figure 4C:
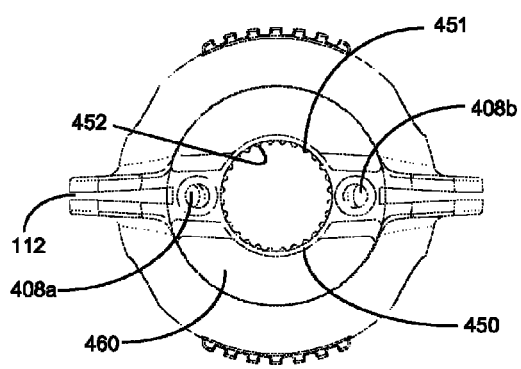
Figure 4D:
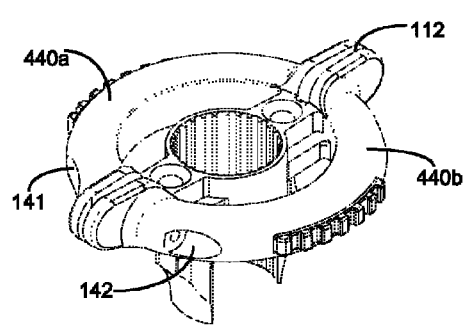

In the arrangement of FIGS. 4A and 4B, needle drive channels 408 are provided with both entry 408*a* and exit 408*b* ports. Differing from previous figures, in this configuration the needle drive channel is configured to be substantially parallel with the longitudinal axis A-A' of the lumen 130. It will be appreciated that the provision of needle guide channels specifically addresses the problems of deploying the olive as an anchoring or suture closure system. In configurations where such anchoring or securing is not required, such drive channels may be dispensed with. The olive—with its expandable housing—will still offer advantages over traditional olives in that it may be used with a plurality of trocars of differing dimensions and will function to assist in the location of the trocar during the surgical procedure.

Figure 4E:
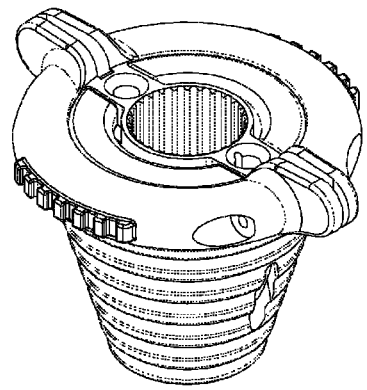
Figure 4F:
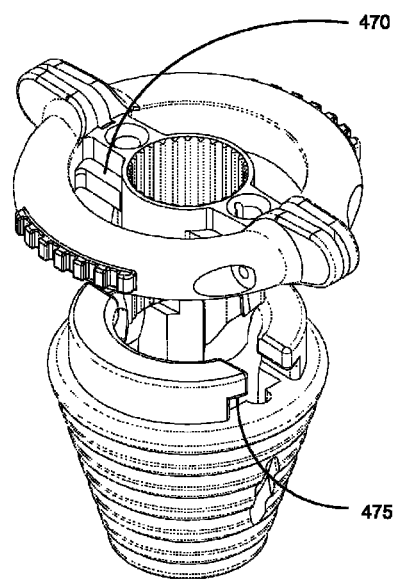

FIGS. 4E and 4F show a further embodiment where an elastomeric sleeve is configured to mate with the olive so that it can be pulled off if not required. Retention clips 475 are mated to a retention face on the olive 470 so that the olive stays connected to the sleeve when a trocar is passed through but can be pulled off if sufficient force is applied by the surgeon. This is particularly advantageous if deploying the device off-midline. It will be appreciated that the clips and corresponding retention face will advantageously obviate the separation of the sleeve from the olive unless a force off parallel to the longitudinal axis of the lumen is applied.

Figure 5A:
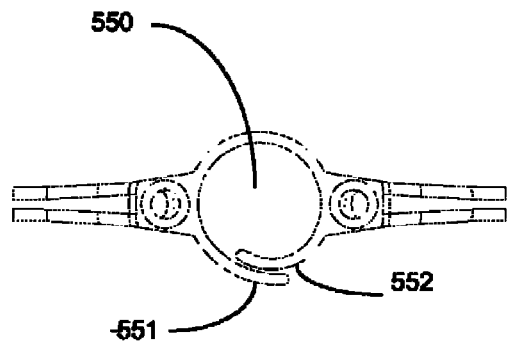
FIGS. 5A and 5B show a further embodiment of an olive which may be used in accordance with the present teaching to provide for a closure of a laparoscopic port with FIG. 5A showing a front elevation view, FIG. 5B a side elevation view of the device from FIG. 5A.
Figure 5B:
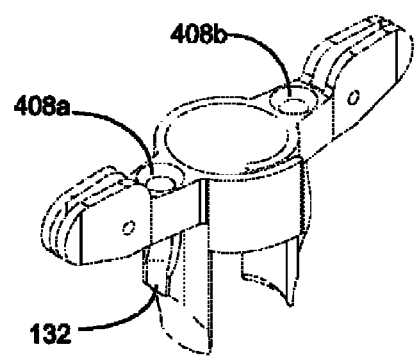

FIGS. 5A and 5B show an alternative arrangement whereby the legs cooperate to form a trocar engaging surface but instead of defining a continuous surface of a trocar engaging lumen 450 such as described in FIGS. 4A to 4D, rather provide a discontinuity formed from overlapping surfaces.

As shown in FIG. 5A, in this configuration a trocar lumen 550 is formed from overlapping surfaces 551, 552 which allows the central lumen to accommodate larger diameter trocars. This arrangement could be manufactured in a variety of different ways such as for example from a rigid polymer, or from a flexible polymer overmoulded on a metal strip in a split ring shape. The metal ring may alternately be a shape memory material, sized to return to the diameter of a minimally sized trocar.

Figure 6:
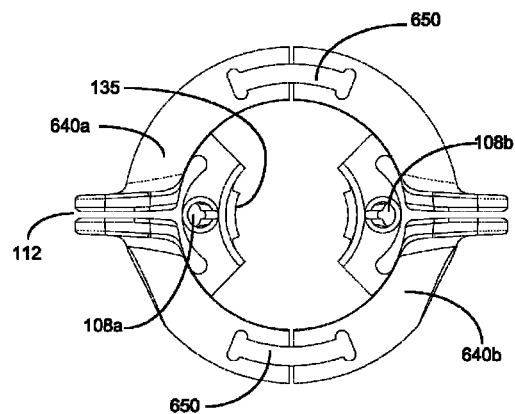
FIG. 6 shows a further embodiment of an olive in plan view which may be used in accordance with the present teaching to provide for a closure of a laparoscopic port.
Figure 7:
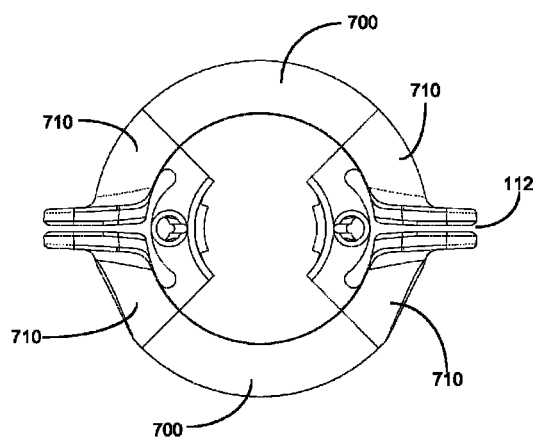
FIG. 7 shows a plan view of a further embodiment of an olive which may be used in accordance with the present teaching to provide for a closure of a laparoscopic port.

FIG. 6 shows another configuration whereby two portions 640*a*, 640*b* are held together by an elastic member 650. In this example the elastic or otherwise resilient member is formed from a dog-bone shaped elastomer or low durometer rubber. When an oversized trocar is passed into the central lumen the elastomer 650 elongates allowing the two halves 640*a*, 640*b* to expand laterally which enlarges the central lumen allowing the trocar to be accommodated FIG. 7 illustrates an alternative to the dog-bone, whereby a low durometer section 700 is attached to a solid section 710. This could be achieved in a number of different ways such as by solvent bonding both materials or by means of overmoulding. It will be appreciated that while the specifics of this illustrated example shows the interface as a flat face, that this may be textured or feature a geometry which increases the surface area or provides a mechanical interlock.

Figure 8:
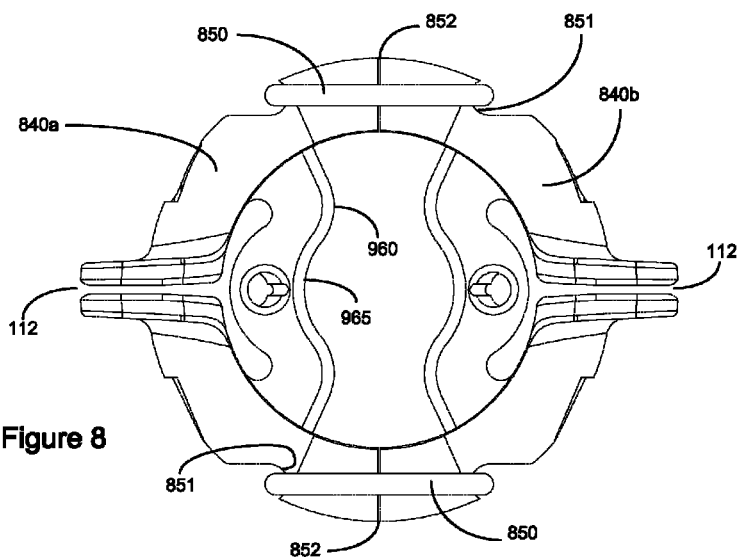
FIG. 8 shows a plan view of a further embodiment of an olive which may be used in accordance with the present teaching to provide for a closure of a laparoscopic port.

FIG. 8 shows another example whereby instead of using an elastomeric dog-bone shaped element to hold two halves of an expandable olive together, the coupling is not integrated into the olive but rather the olive is configured to engage with an o-ring or other elastic member. In this arrangement a pair of o-rings 850 or elastic bands could hold the two halves 840*a*, 840*b* together. In this example, the o-rings are held in a groove feature 851 which is provided on an outer surface of the olive so as to allow a user to place the o-rings onto the olive once the two halves are located relative to one another. On placement, the o-rings are oriented perpendicular to a split 852 between the halves.

In another configuration not shown here, an o-ring could be placed in a groove or other locating feature which encircles the perimeter of the olive, in which case a single o-ring could be used.

Figure 9:
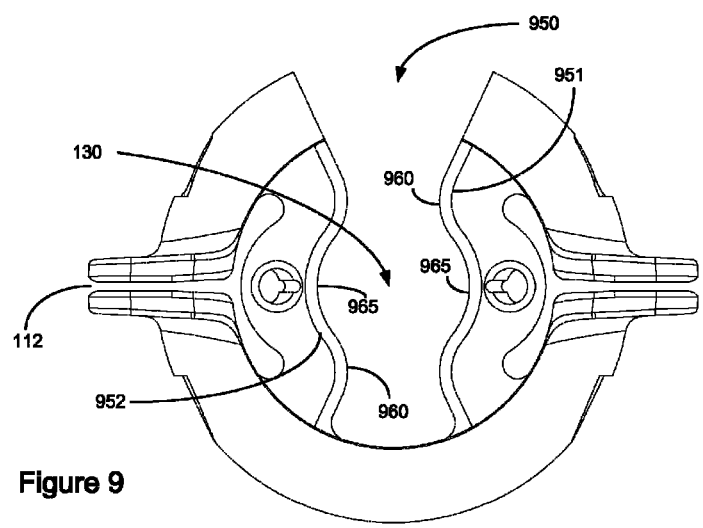
FIG. 9 shows a plan view of a further embodiment of an olive which may be used in accordance with the present teaching to provide for a closure of a laparoscopic port.

FIG. 9 shows an arrangement of an olive which comprises a mouth or cut-out 950 such that the olive extends only partially about the lumen 130 within which the trocar would be located. The cut-out separates two parts of the outer ring of the olive and provides access to the lumen portion of the olive. The parts may then be brought together to close the mouth and tighten the olive about a trocar located therein. By providing such a cut-out, the trocar could be presented to the lumen through a side wall of the olive as opposed to being presented downwardly per the other configurations heretofore described. This can allow the olive to be coupled to the trocar subsequent to the insertion of the trocar through the abdominal wall. In this way the surgeon may elect to use an olive post commencement of the surgery. By presenting the olive sidewardly to the trocar it is possible to locate the trocar within the main housing or body of the olive. Once located it is then possible to slide the olive down the shaft of the trocar to couple the olive to the surgical site after the trocar has already been located within the surgical site. This may advantageously allow the surgeon to elect to use an olive in accordance with the present teaching to effect closure of the wound at any time during the surgery.

An inner portion of the olive comprises opposing curved surfaces 951, 952 which each comprise at least one bump—in the illustrated example two bumps 960 each. The bumps define a concave surface 965 therebetween which is configured to operably cooperate and engage with an outer surface of a trocar. It will be appreciated that dependent on the dimensions of the trocar being used that different parts of the surface 965 may come into contact with the surface of the trocar. Once closing the mouth of the olive and tightening the outer ring, the trocar is secured within the olive. A similar mating surface was shown in the configuration of FIG. 8.

Figure 10A:
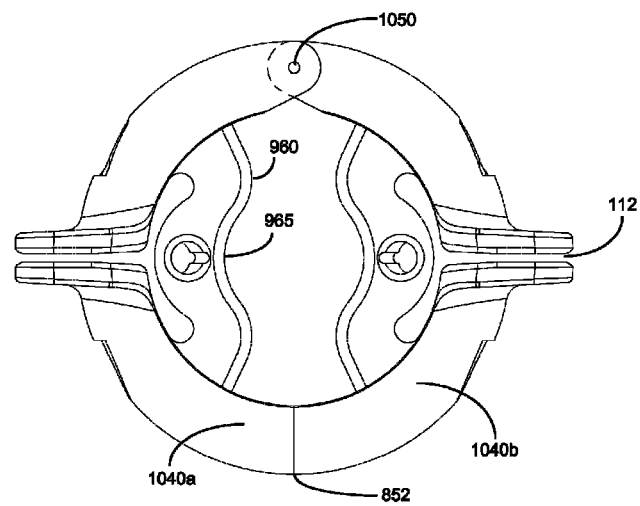
FIGS. 10A and 10B show plan views of a further embodiment of an olive which may be used in accordance with the present teaching to provide for a closure of a laparoscopic port.
Figure 10B:
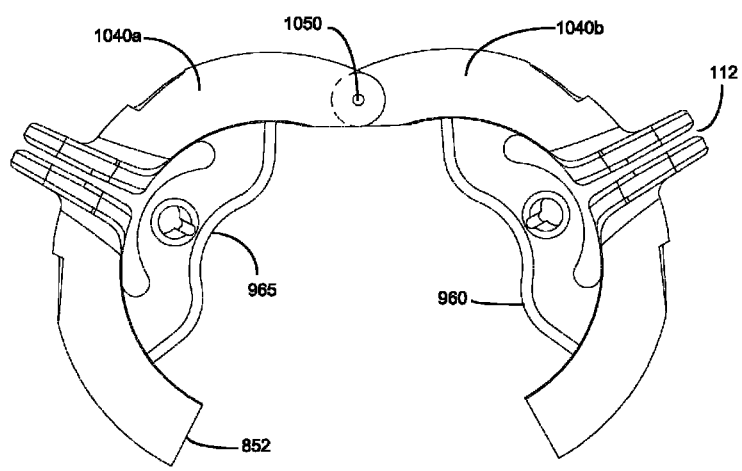
Figure 11B:
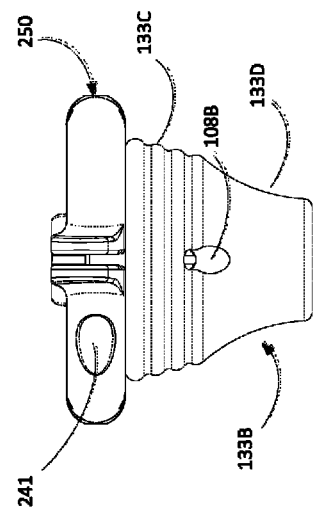
FIGS. 11A to 11D show another example of an olive in accordance with the present teaching.
Figure 11D:
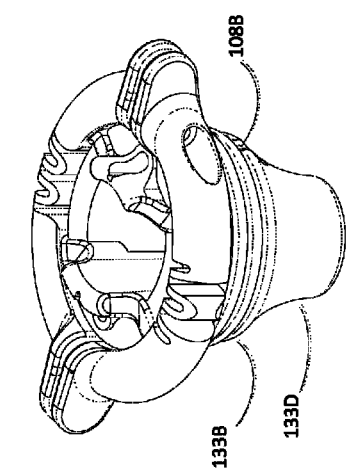
Figure 11A:
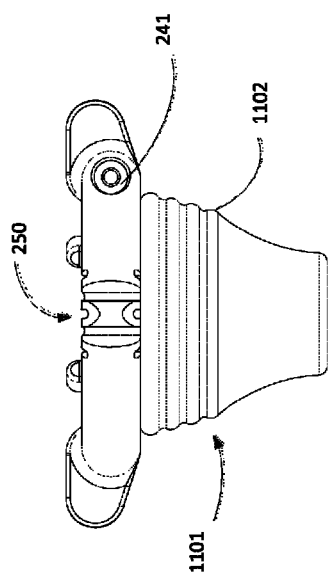
Figure 11C:
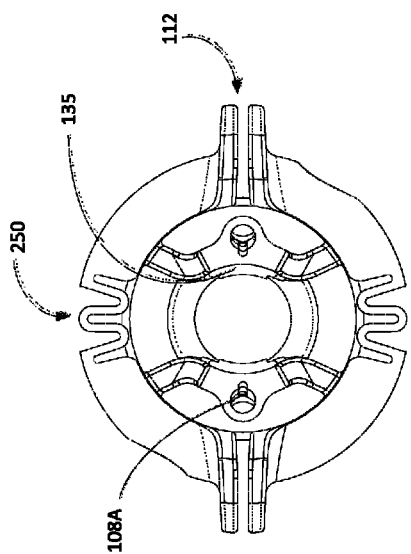
Figure 14E:
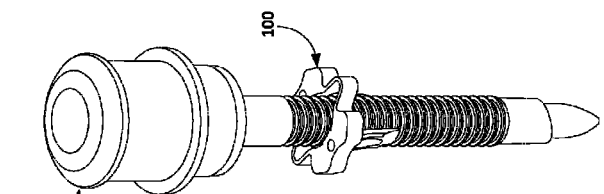
FIGS. 14A to 14E show further examples of operation of a system such as that shown in FIG. 13.
Figure 14D:
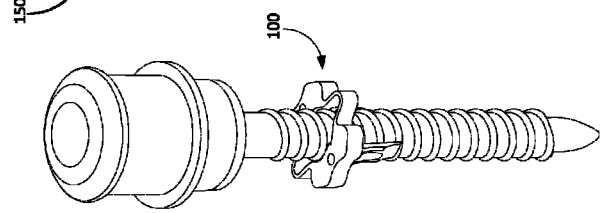
Figure 14C:
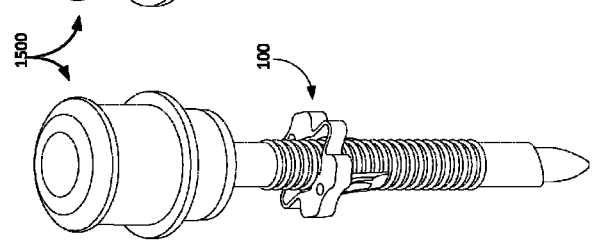
Figure 14B:
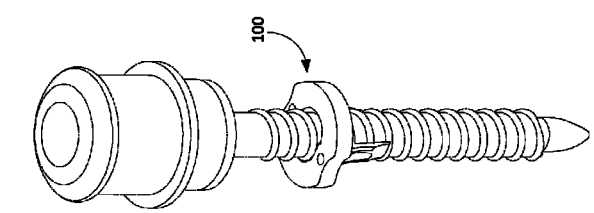
Figure 14A:
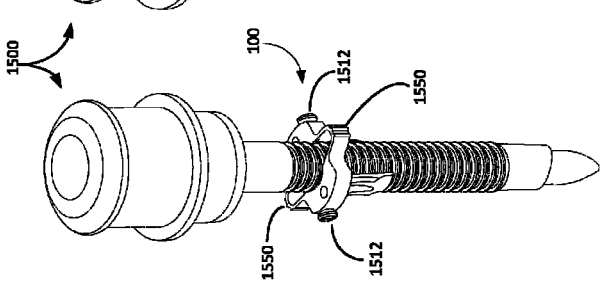

FIG. 10 shows a configuration whereby the olive is formed from first and second parts that are pivotable relative to one another. The two parts of the outer ring 1040*a*, 1040*b* are coupled to one another at a hinge pivot 1050. FIGS. 10A and 10B shows an olive in two halves, with a hinge connecting the halves on one side. FIG. 10*b* shows the halves in an open position. As was discussed above, an advantage of this type of construction is that the olive could be placed on a trocar already in position in the abdomen without removing the trocar. This is especially useful when applied to trocars off midline, where anchoring may not be necessary during the procedure, but closure is required. The halves could be held closed by a clasp or velcro, or a simpler means of a magnet. An alternative method of keeping the two halves together would be placement of a torsion spring at the pivot point.

FIGS. 11A to 11D show a further example of an olive in accordance with the present teaching. Again, the same reference numerals will be used for similar parts. This configuration is most similar to that described above with reference to FIGS. 2A-2D and 3A-3D. As will be seen the sleeve 133B in this configuration comprises an upper 133C and a lower 133D region. The upper region 133C comprises a plurality of ribs 1101 which extend circumferentially about the upper region 133C. These ribs or bumps 1101 act as an tactile indicator to the user of the olive and provide indicative feedback to aid subcutaneous delivery of a needle or indicate the sleeve depth within the tissue.

In contrast to the arrangement of FIG. 2A-2D or 3A-3D, in this configuration the sleeve does not taper at the same angle for its entire length. In this configuration, the upper 133C and the lower 133D region meet at a step 1102. The taper angle changes at the step 1102 and the lower region 133D provides a curved surface, initially curving inwardly towards the lumen. This provides a low profile engagement surface which enables optimal fascial recruitment. The surface of this lower region 133D is smooth.

FIG. 12A-12D shows another arrangement which again uses first and second regions for the sleeve 133E. In this configuration the sleeve 133E is provided having an elliptical geometry-best seen in FIGS. 12A & 12B. It will be appreciated that an ellipse has a major and a minor radius, the minor radius having a smaller length than the major radius. In accordance with the present teaching the sleeve is desirably orientated relative to the first and second parts 240A, 240B such that the needle exit ports exit coincident with the minor radius. The use of such an elliptical sleeve allows optimal fascial recruitment. The material of the sleeve at the major radius provide structure or support to prevent of a flexing of the sleeve when a trocar is presented through the sleeve. In this way the positioning and orientation of the trocar during surgery can be more readily maintained without movement or slippage.

In the configuration of FIGS. 3A-3D, a biasing element was described as being provided by extending the length of the legs so as to provide a projection 350 above the main surface 345 of the outer resting portion 340. In each of FIGS. 11A-11D and 12A-12D, a similar biasing element is provided but in these configurations the projection 350B tapers upwardly and inwardly towards the lumen—i.e. its profile is less than the projection 350 of FIGS. 3A-3D. The needle entry port 108A is again provided in this projection but by providing a raised section, this configuration improves the stability of the device and enables clear visualisation of the guide channels during use.

FIGS. 13A to 18C show examples of olives provided in accordance with the present teaching which are also configured to expand to allow presentation of trocars of varying diameter through the lumen defined by the olives. In these configurations, an inner surface of the olive is provided with one or more locking members or locking surfaces which are configured to operably engage with an outer surface of the presented trocar to minimise relative movement between the two. The same reference numerals will be used for similar parts.

FIG. 13A shows an olive 100 with a trocar locking surfaces 1350 which is shaped or contoured to mate with the contours of the trocar 1500 with which the olive is being used. The trocar locking surfaces in this arrangement are integrally formed or molded with the olive and define an arcuate surface that is concave in shape. In this configuration first and second locking surfaces are provided opposite one another and are biased towards one another. In use these will actively engage with an outer surface of the trocar which is located within the lumen defined by the olive.

This biasing of the inner trocar locking surfaces 1350 is desirably achieved by the same mechanism that provides for an expansion of the olive. In the illustrated examples this is achieved by provision of first and second expansion struts 1550 which are shown in FIG. 15B. The expansion struts are provided opposite one another and are located substantially 90 degrees out of phase with the locking surfaces 1350. In this configuration the outer resting portion 1510 of the olive is expandable due to the addition of expansion struts 1550. These expansion struts allow the inner diameter of the outer resting portion to expand, which in turn allows the trocar locking surfaces 1350 to disengage from the contours of the trocar. In these examples the expansion struts are also integrally formed with the olive body.

The olive of FIG. 13A features a pair of needle entry ports 108 and a pair of suture cleats 1512 (shown in FIG. 14A) as with previous described arrangements. In this configuration, the suture cleat is achieved by a pan head screw, whereby the suture is pulled into space between the pan head of the screw and the surface of the olive adjacent to the screw head. The screw head provides a substantially flat or planar surface and acts as one half of a cleat once tightened against the olive surface, the olive surface acting as the other half of the cleat. The suture can be placed in the clamp between the flat surface of the screw head and the curved surface of the expandable olive by wrapping the suture around the screw head. This improves the capture efficiency. The suture can be wrapped around the screw head until it overlaps with itself to give enhanced securement.

It will be seen that the needle delivery channel 108*a* is angled such that on the initial part 1580 of its trajectory it is angled inwards from the vertical plane, towards the received trocar shaft. This has the advantage of making the needle exit point lower, such that the needle does not have the opportunity to catch at skin level, making the suture entry point lower.

An expandable olive provided in accordance with the present teaching can be used with a variety of different trocar configurations. In the example of FIG. 13A the trocar contours are in the form of annular ridges 1590. These annular ridges, as can be seen in FIG. 13A, taper from a small diameter 1591 to a large diameter 1592, with a step 1593 before the next ridge. This facilitates ease of advancement through the abdominal wall, and provides resistance when the trocar is pulled out, which trocar manufacturers use as a trocar stabilising feature. When the trocar is moved through the olive 100, the trocar locking surfaces 1350 sequentially come into contact with the annular ridges to function as a trocar lock. As the trocar and olive are moved relative to one another such that the trocar progresses through the olive, the change in diameter of the ridges effects a flex in shape of the expandable olive so as to allow the trocar locking surfaces 1350 pass over each ridge, but movement in the opposite direction is prevented by the trocar locking surfaces surface engaging with the step on the trocar. This could advantageously be used to position a trocar in a defect with the olive in the desired location such that it will not be possible for the trocar to pull out of the defect until the olive trocar lock is disengaged.

Anchors may be deployed by advancing a driver through the needle entry ports 108 and then providing for a securement of the suture using the suture cleats 1512. This anchors the olive relative to the abdominal wall and prevents the trocar from being removed. To disengage the trocar lock the user squeezes the expansion struts 1550 together. This is achieved using a pinching movement by the user. The trocar may be freely repositioned within the defect or removed from the olive until the user stops squeezing the expansion struts. Effectively a positive action by the user is required to allow the trocar locks to disengage from the trocar.

FIG. 13B shows a similar arrangement to 13A with an olive on a trocar. Here the trocar contours are in the form of a helical thread 1595. In this instance the olive can be threaded onto the trocar with the trocar locking surfaces 1350 engaging with the trocar thread. It will be appreciated that many rotations of the trocar/or olive may be necessary to position each component in the desired location. To quickly move the trocar relative to the olive the operator will disengage the trocar lock by squeezing the expansion struts 1550 together. This reduces the biasing force that positively moves the locking surfaces into contact with the trocar. The trocar may be repositioned within the defect or removed from the olive. For fine adjustments of the positioning between the olive and trocar, rotation of the trocar could be used.

FIG. 13C shows a similar arrangement to 13A and 13B with an olive on a trocar. Here the trocar contours are in the form of annular rings 1592. In this configuration the annular rings do not taper like the example in FIG. 13A and have radiused corners. The olive will lock on this configuration trocar, but will not be as secure as the embodiments described in FIGS. 13A and 13B.

FIGS. 15A-15B, 16A-16B and 17A-17B show olives which are useable in accordance with the present teaching with different trocars such as those provided with reference numeral 1500 in FIGS. 14A through 14E. FIGS. 15A-15B and 17A-17B are similar in construct in that both contain an expansion strut 1550. In FIG. 17B the expansion strut has a number of raised surfaces 1560 which act as grips when the expansion strut is squeezed or pinched to disengage the trocar lock. The trocar locking surfaces 1350 in FIG. 17A have an increased length over that illustrated in 15A, which has the advantage of giving the retained trocar 1500 increased stability, as it removes some of the degrees of freedom the trocar would otherwise have.

FIGS. 16A and 16B illustrate a similar olive, but with no expansion struts. This could be used where a trocar has less aggressive steps, for example the trocar illustrated in FIG. 13C. It will be appreciated that this olive is also an expandable housing where the locking surfaces are operably biased into contact with a received trocar. However, the absence of the expansion struts, which extend out from the main olive body, reduces the amount of flex that is provided by this arrangement. The olive in this configuration is a more rigid construct than that of FIG. 15A-15B or 17A-17B.

Figure 18C:
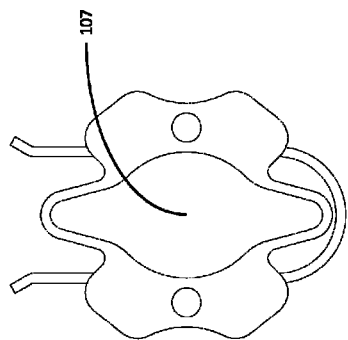
FIGS. 18A to 18C show example of another system comprising a separately formed locking surface which may be used to positively engage with a received trocar.
Figure 18B:
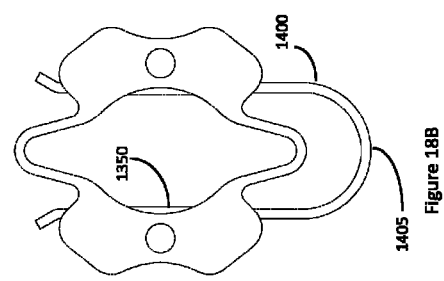
Figure 18A:
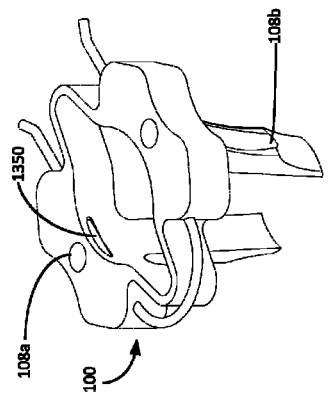

In the arrangement of FIGS. 13A-17B, the engagement surfaces are integrally formed with the olive housing. FIG. 18A to 18C shows another configuration where the trocar locking surfaces 1350 are achieved with a formed wire. In the configuration shown in FIG. 18B the olive will lock onto a trocar. It will be appreciated that the surface of the wire is curved and the wire extends through the expandable housing to define first and second contact points for a received trocar on opposite sides of the lumen.

The wire further defines a curved actuation surface 1405 located externally to the lumen 107. Compression of the curved actuation surface effects a release of the locking surface from a received trocar. It will be appreciated that in the exemplary configuration this compression is effected by pushing the wire towards the olive with the portion 1405. In FIG. 18C the wire is shown pushed forward and the locking surfaces 1350 are disengaged. This could be achieved by having a flat ground on the wire, such that when the wire is in this position none of the wire enter into the lumen 107. It will also be understood that the profile of the wire may be altered to achieve varying degrees of locking. For example a round wire will not lock as securely on a stepped trocar as a square or flat wire profile as the round wire has no edges to catch on the trocar steps. While this embodiment is illustrated as a wire, it will be understood that this illustration is not limiting as this is an example of the type of locking mechanism that can be used to positively engage with a received trocar while not having to be integrally formed or moulded as part of the olive body.

It will be appreciated that by using a locking mechanism such as described in FIGS. 18A and 18B, independent control of the engagement of the locking surfaces relative to the movement of the expandable housing is achieved. The locking surfaces can be brought out of contact from a received trocar without requiring a change in the overall diameter of the lumen, which was not possible with the examples of FIGS. 13A-17B. In this way, while FIGS. 18A and 18B show a trocar lock engagement/disengagement feature with reference to an olive which has an expansion strut, this type of locking feature could also be applied to an olive of the type illustrated in FIGS. 16A and 16B. Again the illustrated trocar lock engagement/disengagement feature is illustrated as a wire, but this could also be a plastic profile which achieves the same goal. Alternately a profile could also be created which when turned circumferentially will function like a cam to create a trocar locking surface.

While the olive of the present teaching has been described with reference to a needle driver and anchoring system it will be appreciated that an olive which can be used with trocars of differing dimensions may not necessarily be deployed in scenarios that require anchoring. As such the provision of features that assist in the anchoring of the olive or the closure of a wound post-surgery should not be considered as essential to the present teaching. It will be appreciated that the word trocar when used in the context of the present teaching should not be limited to a sharp-pointed surgical instrument fitted with a cannula and used especially to insert the cannula into a body cavity as a drainage outlet. The term trocar when used in the context of the present teaching is intended to define generally a surgical instrument that is used in laparoscopic surgery to allow surgical access within the abdominal cavity through a port provided in the abdominal wall and can include the cannula that functions as that portal.

While the olive may be fabricated from any suitable material, the present inventors have ascertained that fabrication from a polypropylene such as the medium melt-flow-rate polypropylene homopolymer prepared by Borealis Nucleation Technology (BNT) and sold under the trademark Bormed HD850MO™ is particularly advantageous. This grade of material is found to have the flexibility of generic polypropylenes but is also more impact resistant and harder than most polypropylene grades which enables the flexibility of the hinge/movement function but also is less susceptible to damage when used with threaded trocars which chafe material off softer grades in use. Details of the properties of this polypropylene are provided below:

| Physical Properties | Typical Value | Test Method |
|---|---|---|
| Density | 910 kg/m$^3$ | ISO 1183 |
| Melt Flow Rate (230° C./2.16 kg) | 8 g/10 min | ISO 1133 |
| Tensile Modulus (1 mm/min) | 1.800 MPa | ISO 527-2 |
| Tensile Strain at Yield (50 mm/min) | 7.5% | ISO 527-2 |
| Tensile Stress at Yield (50 mm/min) | 38 MPa | ISO 527-2 |
| Heat Deflection Temperature (0.45 MPa) | 112° C. | ISO 75-2 |
| Charpy Impact Strength, notched (23° C.) | 5.5 kJ/m$^2$ | ISO 179/1eA |
| Hardness, Rockwell (R-scale) | 105 | ISO 2039-2 |

While preferred arrangements have been described in an effort to assist in an understanding of the teaching of the present invention it will be appreciated that it is not intended to limit the present teaching to that described and modifications can be made without departing from the scope of the invention.

It will be appreciated that the exemplary arrangements or examples of devices have been described with reference to the Figures attached hereto. Where a feature or element is described with reference to one Figure, it will be understood that the feature or element could be used with or interchanged for features or elements described with reference to another Figure or example. The person of skill in the art, when reviewing the present teaching, will understand that it is not intended to limit the present teaching to the specifics of the illustrated exemplary arrangements as modifications can be made without departing from the scope of the present teaching.

The words comprises/comprising when used in this specification are to specify the presence of stated features, integers, steps or components but does not preclude the presence or addition of one or more other features, integers, steps, components or groups thereof.

The invention claimed is:

1. A laparoscopic system configured for engagement with an aperture provided in an abdominal wall, the system comprising:
    an expandable housing defining a lumen for receipt and delivery of a trocar into an abdominal cavity, the housing comprising an outer resting portion which in use is configured to rest against an outer surface of the abdominal wall, the outer resting portion comprising a first part and a second part which are moveable relative to each other, the outer resting portion being arranged to extend circumferentially about the lumen to define a path which defines an entry port through which the trocar can be presented into the lumen to pass into the abdominal cavity;
    a first needle guide channel and a second needle guide channel defined within an abdominal wall engaging portion of the housing, the first needle guide channel and the second needle guide channel being provided on opposite sides of the lumen respectively and each needle guide channel having an entry port located proximal the outer resting portion and dimensioned to operably receive a needle driver and an exit port, located above a distal end portion of the abdominal wall engaging portion and through which the needle driver operably exits the needle guide channel and enters directly into the abdominal wall, the needle guide channels operably allowing the delivery of suture or an anchor through the housing and directly into the abdominal wall, wherein the needle guide channels and lumen are separate and distinct such that suture does not operably pass through the lumen on delivery through the system; and
    wherein an expansion of the housing by relative movement of the first part and the second part varies a length of the path to operably accommodates trocar of different dimensions while maintaining the first needle guide channel and the second needle guide channel substantially opposite to one another irrespective of the length of the path.

2. The system of claim 1 wherein the needle guide channels comprise a convex surface proximal to the lumen such that the suture will exit away from the lumen on being displaced out of the needle guide channels.

3. The system of claim 1 wherein the outer resting portion operably defines a complete collar, the trocar operably being presented through the collar and into the lumen in a direction parallel to its longitudinal axis.

4. The system of claim 3 wherein the first and second part are secured to one another using a securing member which mates with each of the first and second parts.

5. The system of claim 4 wherein the securing member is received within a body portion of the first and second parts.

6. The system of claim 4 wherein the securing member is secured about an exterior surface of the first and second parts.

7. The system of claim 4 wherein the securing member comprises first and second securing members which are operably located on opposing sides of the lumen.

8. The system of claim 4 wherein the first and second parts are hinged relative to one another.

9. The system of claim 1 wherein the first and second part are separate to each other.

10. The system of claim 9 wherein the first and second part define a mouth therebetween through which the trocar may be presented into the lumen in a direction transverse to a longitudinal axis of the lumen.

11. The system of claim 1 wherein the housing is provided in a multi-part construction comprising first and second lumen defining parts that are co-operable with one another to define the lumen.

12. The system of claim 11 wherein on bringing the first and second lumen defining parts together the housing defines a continuous inner surface which operably engages with the trocar.

13. The system of claim 11 wherein on bringing the first and second lumen defining parts together the housing defines a discontinuous inner surface which operably engages with the trocar.

14. The system of claim 13 wherein the first and second lumen defining parts overlap with one another.

15. The system of claim 11 wherein the first and second lumen defining parts are at least partially flexible.

16. The system of claim 15 wherein the first and second lumen defining parts are at least partially corrugated.

17. The system of claim 1 wherein the housing comprises a continuous surface formed from a single piece which operably provides a contact surface for engaging with the trocar.

18. The system of claim 17 wherein the single piece is at least partially corrugated to improve the flexibility of the piece.

19. The system of claim 1 comprising a flexible sleeve.

20. The system of claim 19 wherein the flexible sleeve comprises an outer and an inner surface, the outer surface operably defining a portion configured to contact the abdominal wall.

21. The system of claim 20 wherein the sleeve is expandable to accommodate trocars of different dimensions.

22. The system of claim 21 wherein the sleeve defines a ring through which the trocar may operably pass, the ring having a diameter corresponding substantially with the smallest diameter of instrumentation with which the system is intended for use.

23. The system of claim 22 wherein the ring is configured to expand to accommodate a trocar of larger diameter.

24. The system of claim 22 wherein the sleeve has a first and second configuration, wherein in the first configuration the outer surface tapers inwardly towards the ring.

25. The system of claim 24 wherein in the second configuration the outer surface comprises a first region that tapers inwardly towards the ring and a second region substantially parallel with a longitudinal axis of the lumen.

26. The system of claim 19 wherein the sleeve comprises a ribbed surface.

27. The system of claim 19 wherein the sleeve is operably engageable with and removable from the outer resting portion.

28. The system of claim 27 wherein the sleeve comprises retention clips which operably couple with the outer resting portion and allow the sleeve be pulled away from the outer resting portion on application of a force by the surgeon.

29. The system of claim 27 wherein the sleeve comprises projection surfaces which are receivable within a volume defined by the outer resting portion and prevent the sleeve rotating relative to the outer resting portion.

30. The system of claim 29 wherein the projection surfaces pinchably engage with the outer resting portion.

31. The system of claim 19 whereby the sleeve comprises a sealing and trocar retention ring which accommodates a variety of trocar diameters and trocar surface finishes.

32. The system of claim 19 wherein the sleeve comprises an upper and lower region, the upper region comprises a ribbed outer surface and the lower region a smooth outer surface.

33. The system of claim 32 wherein the lower region is tapered at a different angle to the upper region.

34. The system of claim 19 wherein the sleeve is elliptical.

35. The system of claim 34 wherein needle exit ports are provided within the sleeve parallel to a minor radius of the ellipse defining the sleeve.

36. The system of claim 19 wherein the sleeve comprises a sealing surface which provides a curved surface extending circumferentially about the housing and which in use is configured to be located against the abdominal wall.

37. The system of claim 19 wherein the sleeve extends inwardly from the resting portion and is defined by a hollow conical structure having side walls that taper inwardly.

38. The system of claim 19 wherein the sleeve comprises one or more engagement surfaces provided on an outer surface thereof, the engagement surface configured to operably provide anchoring against the abdominal wall.

39. The system of claim 19 comprising legs, the sleeve being receivable over the legs.

40. The system of claim 39 wherein the legs comprise a biasing element that projects above an upper surface of the first and second parts.

41. The system of claim 1 comprising a suture securement feature for securing a suture relative to the housing.

42. The system of claim 41 wherein the suture securement feature comprises two opposing faces which when brought together form a clamp.

43. The system of claim 1 wherein the outer resting portion comprises first and second cut-away portions provided in faces transverse to the exit ports of the needle guide channels, the cut-away portions defining a tissue invagination zone within the abdominal wall engaging portion into which tissue may extend inwardly towards the lumen.

44. The system of claim 1 further comprising expansion struts configured to allow an expansion of the outer resting portion.

45. The system of claim 1 wherein each of the first part and the second part comprise expansion struts which operably extend linearly and advantageously allows for each of the two parts to expand to the same level so as to retain a level of symmetry about the lumen.

46. The system of claim 1 wherein the housing comprises at least one adhesive pad.

47. The system of claim 1 further comprising at least one locking surface configured to operably engage with a received trocar.

48. The system of claim 47 wherein the expandable housing is configured to bias the at least one locking surface into positive contact with the received trocar.

49. The system of claim 48 comprising at least one expansion strut, the at least one expansion strut being operably pinchable by an operator to facilitate disengagement of the locking surface from the received trocar.

50. The system of claim 49 comprising first and second expansion struts provided on opposite sides of the lumen to one another.

51. The system of claim 47 wherein the expandable housing comprises first and second locking surfaces provided on opposite sides of the lumen.

52. The system of claim 51 wherein each of the first and second locking surfaces comprise an arcuate surface which operably contacts an outer surface of the trocar.

53. The system of claim 47 wherein the at least one locking surface is integrally formed with the expandable housing.

54. The system of claim 47 wherein the at least one locking surface is formed separately to the expandable housing.

55. The system of claim 54 wherein the at least one locking surface comprises a curved surface.

56. The system of claim 54 wherein the at least one locking surface comprises a wire.

57. The system of claim 56 wherein the wire extends through the expandable housing to define first and second contact points for the received trocar on opposite sides of the lumen.

58. The system of claim 57 wherein the wire defines a curved actuation surface located externally to the lumen.

59. The system of claim 58 wherein compression of the curved actuation surface effects a release of the locking surface from the received trocar.

60. The system of claim 47 wherein the locking surface is activated by rotation of a cam surface.

\* \* \* \* \*